United States Patent
Dietrich et al.

(10) Patent No.: US 11,001,098 B2
(45) Date of Patent: May 11, 2021

(54) MOBILE MEDICAL DEVICE WITH AT LEAST ONE MOTOR-DRIVEN WHEEL

(71) Applicants: Florian Dietrich, Baiersdorf (DE); Franz Dirauf, Ebensfeld (DE)

(72) Inventors: Florian Dietrich, Baiersdorf (DE); Franz Dirauf, Ebensfeld (DE)

(73) Assignee: Siemens Healthcare GmbH, Erlangen (DE)

(*) Notice: Subject to any disclaimer, the term of this patent is extended or adjusted under 35 U.S.C. 154(b) by 528 days.

(21) Appl. No.: 15/566,477

(22) PCT Filed: Mar. 24, 2016

(86) PCT No.: PCT/EP2016/056515
§ 371 (c)(1),
(2) Date: Oct. 13, 2017

(87) PCT Pub. No.: WO2016/165925
PCT Pub. Date: Oct. 20, 2016

(65) Prior Publication Data
US 2018/0297396 A1    Oct. 18, 2018

(30) Foreign Application Priority Data
Apr. 16, 2015  (DE) .......................... 102015206909.5

(51) Int. Cl.
*B60B 3/14*   (2006.01)
*B60B 19/00*  (2006.01)
(Continued)

(52) U.S. Cl.
CPC .............. *B60B 3/14* (2013.01); *A61G 13/104* (2013.01); *B60B 3/147* (2013.01); *B60B 3/165* (2013.01);
(Continued)

(58) Field of Classification Search
CPC ........... B60B 3/14; B60B 3/142; B60B 3/147; B60B 3/18; B60B 3/165; B60B 19/003;
(Continued)

(56) References Cited

U.S. PATENT DOCUMENTS 2,026,586 A * 1/1936 McVeagh .................. B60B 3/18
                                                    301/35.56
3,944,285 A * 3/1976 Vincent ..................... B60B 3/14
                                                    301/35.621
(Continued)

FOREIGN PATENT DOCUMENTS

CN    201287583 Y    8/2009
CN    201494299 U    6/2010
(Continued)

OTHER PUBLICATIONS

German Office Action for related German Application No. 10 2015 206 909.5 dated Nov. 2, 2015.
(Continued)

*Primary Examiner* — Scott A Browne
(74) *Attorney, Agent, or Firm* — Lempia Summerfield Katz LLC (57) ABSTRACT

The present embodiments provide a mobile medical device with at least one motor-driven wheel. The mobile medical device is movable on the at least one wheel. The motor-driven wheel is arranged on a hub assigned to the motor-driven wheel. The motor-driven wheel is reversibly removable from the hub and is pluggable back onto the hub manually and without aids. The present embodiments provide that the motor-driven wheel may be removed rapidly manually and without additional aids.

20 Claims, 5 Drawing Sheets

(51) Int. Cl.
*B60K 7/00* (2006.01)
*B60B 3/16* (2006.01)
*A61G 13/10* (2006.01)
B60B 37/10 (2006.01)
B60B 3/18 (2006.01)
A61G 7/08 (2006.01)
A61G 7/018 (2006.01)
A61G 7/05 (2006.01)
A61B 6/00 (2006.01)
B60B 7/00 (2006.01)

(52) U.S. Cl.
CPC .......... *B60B 19/003* (2013.01); *B60K 7/0007* (2013.01); *A61B 6/4405* (2013.01); *A61B 6/4441* (2013.01); *A61G 7/018* (2013.01); *A61G 7/05* (2013.01); *A61G 7/08* (2013.01); *B60B 3/18* (2013.01); *B60B 7/00* (2013.01); *B60B 37/10* (2013.01); *B60B 2200/26* (2013.01); *B60B 2900/211* (2013.01); *B60B 2900/541* (2013.01); *B60K 2007/0038* (2013.01); *B60K 2007/0092* (2013.01)

(58) Field of Classification Search
CPC ................ B60B 37/10; B60B 2200/26; B60B 2900/211; B60B 2900/541; A61G 13/104; A61G 13/04; A61B 6/4405; A61B 6/4441; B60K 7/0007
See application file for complete search history.

(56) References Cited

U.S. PATENT DOCUMENTS

| | | | | |
|---|---|---|---|---|
| 4,347,907 A * | 9/1982 | Downing, Jr. | ............ | B60K 6/24 180/65.1 |
| 4,664,252 A * | 5/1987 | Galbraith | ............... | B65G 39/12 193/37 |
| 6,044,921 A * | 4/2000 | Lansberry | .............. | B60G 11/02 180/9.36 |
| 6,173,481 B1 * | 1/2001 | Parent | .................. | B60B 29/001 29/273 |
| 6,813,939 B1 * | 11/2004 | Wilcoxon | ......... | G01M 17/0074 73/146 |
| 8,549,705 B1 | 10/2013 | Wu | | |
| 2004/0061373 A1 * | 4/2004 | McPherson | ........... | B60P 3/1066 301/8 |
| 2007/0035106 A1 * | 2/2007 | Thorpe | ..................... | B60B 3/14 280/260 |
| 2008/0169140 A1 * | 7/2008 | Perry | ..................... | H02K 21/12 180/65.51 |
| 2009/0051184 A1 | 2/2009 | Saleem | | |
| 2011/0306864 A1 | 12/2011 | Zarate | | |
| 2014/0054952 A1 | 2/2014 | Krell | | |
| 2014/0379130 A1 * | 12/2014 | Lee | ........................... | B62D 1/02 700/259 |
| 2020/0008990 A1 * | 1/2020 | Harrison | ................ | B62K 5/007 |

FOREIGN PATENT DOCUMENTS

| | | |
|---|---|---|
| CN | 102274076 A | 12/2011 |
| CN | 203226834 U | 10/2013 |
| CN | 203698407 U | 7/2014 |
| CN | 204172612 U | 2/2015 |
| DE | 19949408 C1 | 10/2000 |
| JP | S4426357 Y1 | 11/1969 |
| JP | S4612813 Y1 | 5/1971 |
| JP | 3009470 U | 4/1995 |
| JP | 2002046670 A | 2/2002 |
| JP | 2004176874 A | 6/2004 |
| JP | 2005067334 A | 3/2005 |
| WO | WO2006037935 A1 | 4/2006 |
| WO | WO2015119999 A1 | 8/2015 |
| WO | WO2015120000 A1 | 8/2015 |

OTHER PUBLICATIONS

PCT International Search Report and Written Opinion of the International Searching Authority dated Jul. 7, 2016 for corresponding PCT/EP2016/056515.
Chinese Office Action for Chinese Application No. 201680022264.4 dated Aug. 22, 2019.
Chinese Office Action for Chinese Application No. 201680022264.4 dated Feb. 27, 2020.
Japanese Office Action for Japanese Application No. 2017-554044 dated Feb. 4, 2020, with English translation.

* cited by examiner

MOBILE MEDICAL DEVICE WITH AT LEAST ONE MOTOR-DRIVEN WHEEL

CROSS-REFERENCE TO RELATED APPLICATIONS

This application is the National Stage of International Application No. PCT/EP2016/056515, filed Mar. 24, 2016, that claims the benefit of German Patent Application No. DE 10 2015 206909.5, filed Apr. 16, 2015. The entire contents of these documents are hereby incorporated herein by reference.

TECHNICAL FIELD

The present embodiments relate to a mobile medical device that may be moved on a floor surface with the aid of motor-driven wheels. For example, the medical device may be a patient support or a C-arm X-ray device.

BACKGROUND

Mobile medical devices typically have a chassis with manually or motor-driven wheels and are used in medical domains (e.g., in operating rooms). The floor surface may be soiled in such an environment (e.g., by bodily fluids, rinsing liquids or consumable materials).

For example, published application US 20140379130 A1 discloses use of Mecanum wheels for mobile medical devices. Due to good maneuverability, Mecanum wheels are suitable for use in the clinical domain.

The Mecanum wheel is a wheel permitting a vehicle to make omnidirectional maneuvers without having to be provided with a mechanical steering system. Mounted on the circumference of the wheel are a plurality of rotatably mounted barrel-shaped rollers (e.g., such as at an angle of 45 degrees to the axle of the whole wheel). Only the barrel-shaped rollers make contact with the floor surface. The barrel-shaped rollers have no direct drive and may rotate freely about their inclined bearing axis. The whole Mecanum wheel is driven by a drive motor with an adjustable rotation direction and a variable rotary speed. In order to realize the omnidirectional maneuver, the rotary speed and the rotation direction of each wheel is controlled individually.

In the utility model specification CN 203226834 U, a mobile C-arm X-ray device with omnidirectional wheels is disclosed and individual control of each wheel is described.

Motor-driven wheels and omnidirectional wheels, such as Mecanum wheels, are difficult to clean due to their structure or their fastening. It is usual to clean the floor and the equipment in an operating room by wiping, subjecting the floor and the equipment to a particularly thorough cleaning and disinfection at particular time intervals. Thorough cleaning of the wheels is difficult.

To facilitate the use of mobile medical devices, such as C-arm X-ray devices and mobile patient supports (e.g., during surgical interventions), measures for reducing the contamination risk of the mobile medical devices are to be taken.

SUMMARY AND DESCRIPTION

The scope of the present invention is defined solely by the appended claims and is not affected to any degree by the statements within this summary.

One or more of the present embodiments may obviate one or more of the drawbacks or limitations in the related art. For example, a mobile medical device is provided with motor-driven wheels that may be used in a contaminated environment.

According to the present embodiments, a mobile medical device is provided having at least one motor-driven wheel.

According to an embodiment, the motor-driven wheel is configured such that the motor-driven wheel may be removed from and replaced in a rotatable hub of the mobile medical device with bare hands (e.g., by hand and without aids, such as tools).

An embodiments provides a mobile medical device with at least one motor-driven wheel for moving the mobile medical device. The motor-driven wheel is arranged on a hub belonging to the motor-driven wheel, and may be reversibly removed from the hub and reversibly placed on the hub by hand and without aids.

The present embodiments provide that, for cleaning purposes, the motor-driven wheel may very easily be removed from the medical device and cleaned (e.g., in a suitable washing and disinfecting device).

In an embodiment, the motor-driven wheel is configured as an omnidirectional wheel.

In an embodiment, the hub is rotatably mounted on an axle of the mobile medical device.

In another embodiment, the motor-driven wheel has a locking device for firmly fastening the motor-driven wheel to the hub releasably and released from the hub.

In an embodiment, grooves may be arranged on the circumference of the hub and corresponding guide elements of the locking device may engage in these grooves, with the locking device configured to be rotatable.

In another embodiment, the rotatable locking device has grooves and corresponding guide elements engaging in the grooves arranged on the circumference of the hub.

The locking device may include a fold-out gripping element arranged on the end face of the motor-driven wheel facing away from the medical device.

In another embodiment, the locking device and the hub may be configured such that the gripping element may be folded in only in a locked position of the motor-driven wheel.

In another embodiment, the medical device has a protective sheet metal-like cover element that may be folded over the motor-driven wheel. The cover element may be folded only when in a locked position of the motor-driven wheel.

In another embodiment, the mobile medical device has a lifting apparatus that may lift the motor-driven wheel from a floor surface.

In another embodiment, an electric motor for driving the motor-driven wheel is arranged in the axle.

The mobile medical device may also have at least one non-motor-driven further wheel with which the mobile medical device may be moved with a raised motor-driven wheel.

In another embodiment, the mobile medical device has at least four omnidirectional wheels wherein these are configured as Mecanum wheels.

In another embodiment, the hub is configured to be truncated cone-shaped and the motor-driven wheel has a corresponding truncated conical depression.

In another embodiment, at least one twist-proofing element is arranged on the circumference of the hub, holding the motor-driven wheel in a twist-proof manner on the hub.

DETAILED DESCRIPTION

Figure 1:
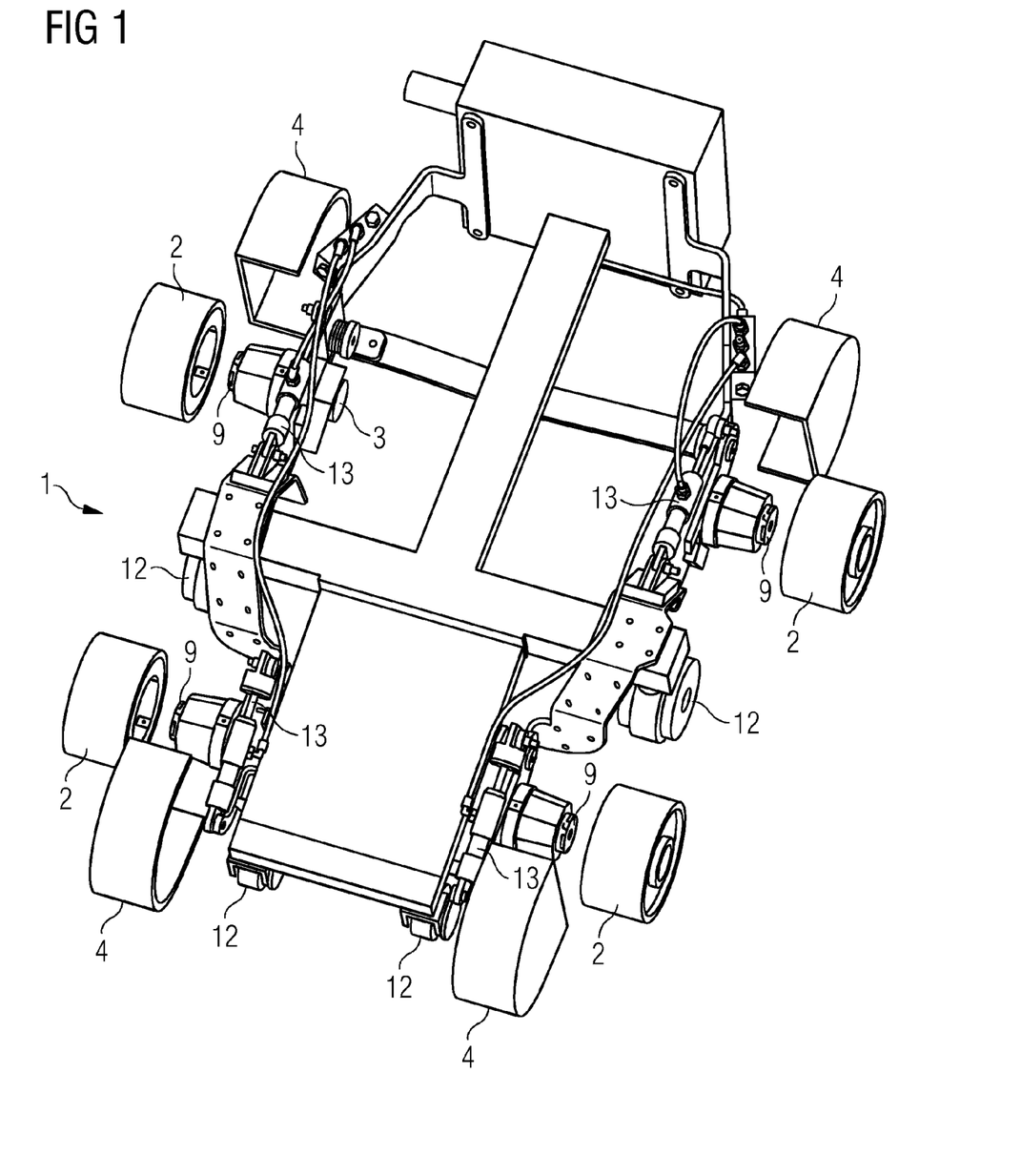
FIG. 1 depicts an embodiment of a mobile medical device with at least one motor-driven wheel.

FIG. 1 shows a mobile medical device 1 with at least one motor-driven wheel 2. In this exemplary embodiment, the mobile medical device 1 has four wheels 2 that are each motor-driven by a dedicated electric motor 3.

In this embodiment, a protective sheet metal-like foldable cover element 4, visible in an opened position, is arranged over the motor-driven wheel 2. In the closed position (e.g., the folded-down position), the cover element 4 may act in a soil-repelling manner and also as a cable deflector.

FIG. 1 also shows the mobile medical device 1 with a lifting apparatus 13 of the motor-driven wheels 2 and with four further wheels 12 that are not motor-driven.

To be able to carry out a wheel change rapidly and without additional aids, each motor-driven wheel 2 has a lifting apparatus 13. Thus, each motor-driven wheel 2 may be raised individually from a floor surface. When a wheel is changed, the mobile medical device 1 supports itself on the floor on the remaining non-raised motor-driven wheels 2. For example, in this embodiment (not shown), no additional wheels 12 supports are needed.

In another embodiment, all the motor-driven wheels 2 may be raised by the raising apparatuses 13 from the floor surface simultaneously. The mobile medical device 1 has a further, second wheel set including at least two non-motor-driven wheels 12 or supports on which the mobile medical device 1 may support itself on the floor surface. The raised motor-driven wheels 2 are therefore situated clear and may be removed.

In another embodiment, the lifting apparatus 13 is configured such that the motor-driven wheels 2 that are to be changed remain at an unchanged height relative to a chassis of the mobile medical device 1. A person skilled in the art in the present field of technology would understand a chassis to be the totality of all parts of a movable device serving for the connection of the superstructure of the movable device by the wheels 2 to the movement surface (e.g., motor-driven wheels). Here, the entire chassis may be raised from the floor surface with the aid of additional wheels 12 or supports.

In an embodiment, the mobile medical device 1 has a second wheel set (e.g., at least three non-motor-driven further wheels 12), providing, in the event of a failure of the motor drive by the electric motors 3 of the motor-driven wheels 2, that the mobile medical device 1 nevertheless may be moved and the second wheel set is therefore relevant to safety.

In an exemplary embodiment (not shown), the mobile medical device 1 has four motor-driven wheels 2 in the form of omnidirectional wheels 15 (e.g., Mecanum wheels). With Mecanum wheels, the rotation direction and the rotary speed of each individual wheel is controlled separately. This offers the advantage of an optimum maneuverability (e.g., in tight spaces, as is often the case in operating rooms).

Figure 2:
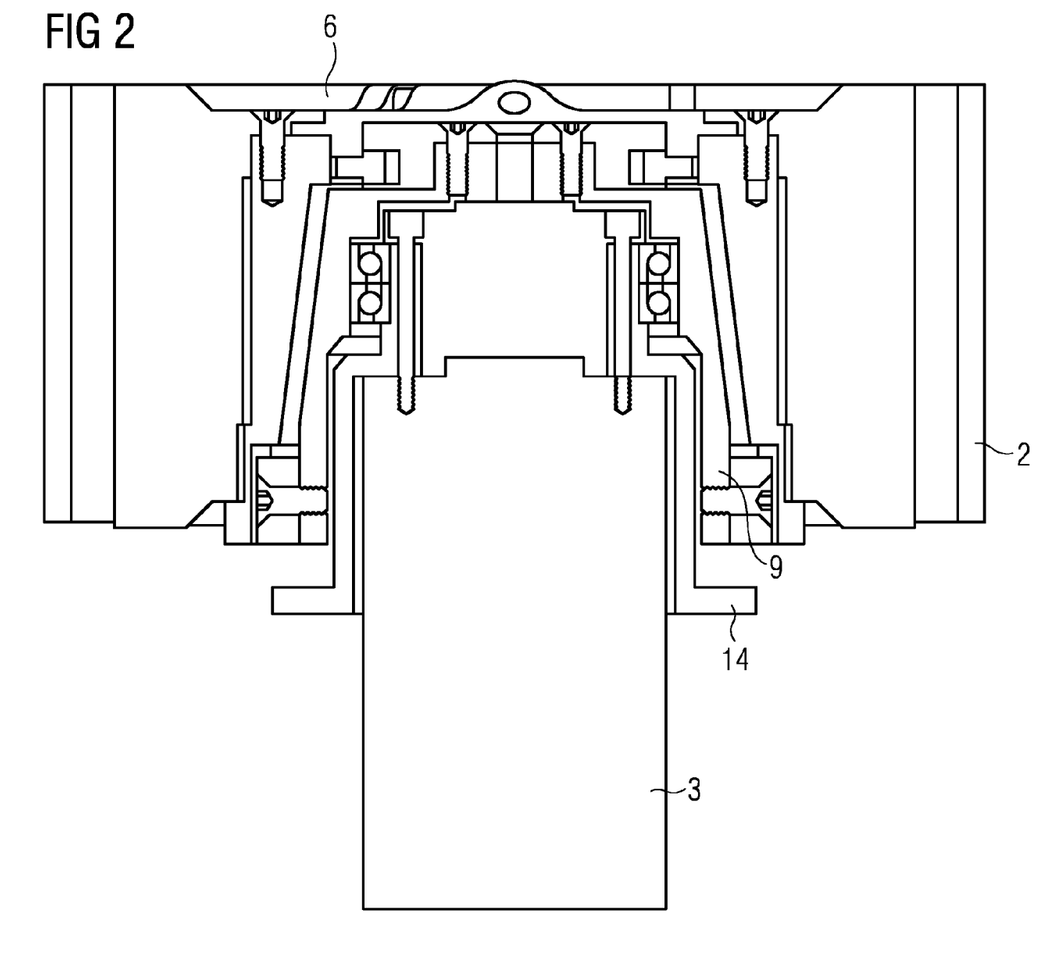
FIG. 2 depicts an embodiment of a motor-driven wheel in an axial sectional view.

FIG. 2 shows the motor-driven wheel 2, the hub 9, the axle 14 and the electric motor 3 in axial section. The electric motor 3 in the embodiment shown is situated in the axle 14, which is configured as a hollow axle or also as a tube. Each motor-driven wheel 2 is arranged on a hub 9 associated with this motor-driven wheel 2 and is rotatably mounted on the axle 14. Rotatably mounting the motor-driven wheel 2 on the axle 14 may be carried out by wheel bearings (e.g., in the form of ball bearings). The electric motor 3 thus drives the hub 3 via a gearbox and one or more catches (e.g., by driver pins or known other ways of implementing a catch), the hub transmitting torque to the motor-driven wheel 2.

Figure 3:
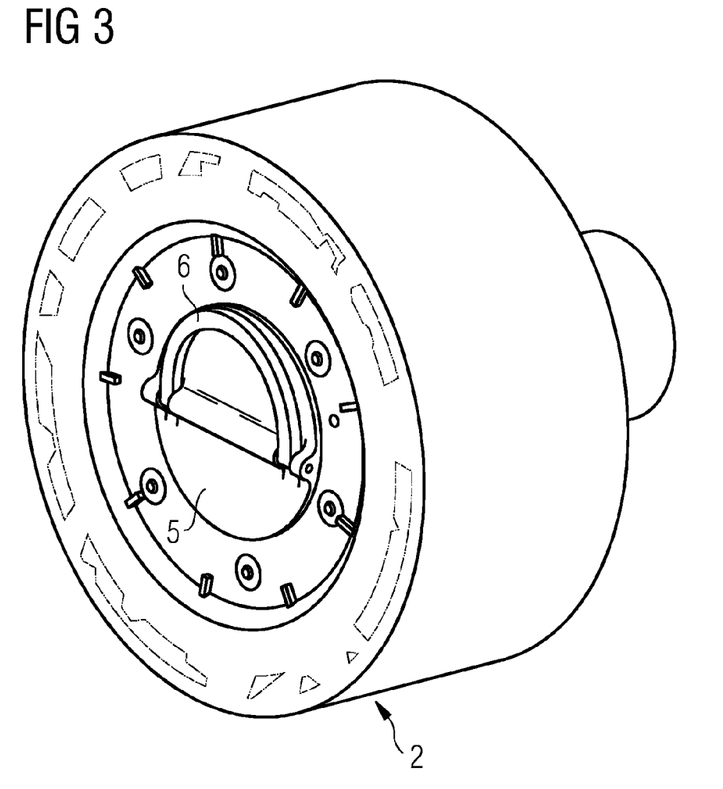
FIG. 3 depicts an embodiment of a motor-driven wheel in an external view.

FIG. 3 shows a motor-driven wheel 2 in an external view. The motor-driven wheel 2 has a locking device 5 concentrically integrated into the motor-driven wheel 2. The locking device 5 includes a fold-out gripping element 5 on the end side.

Figure 4:
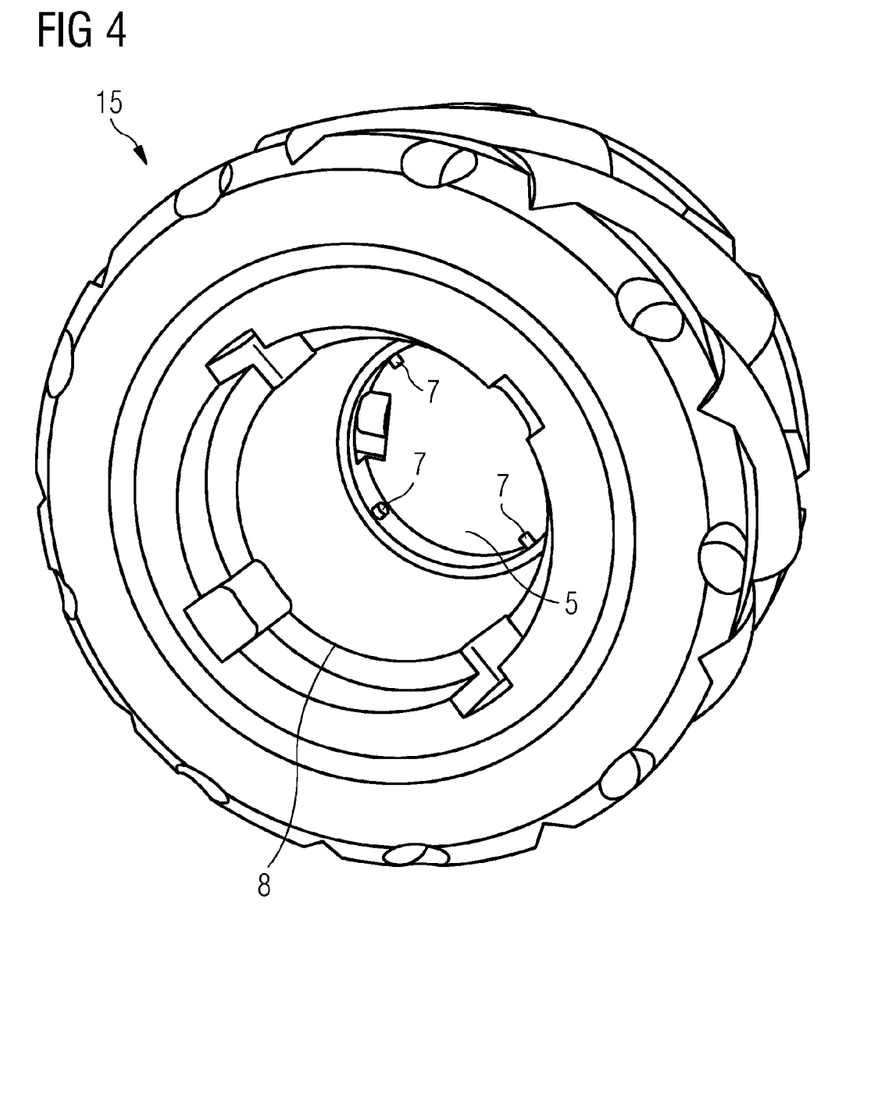
FIG. 4 depicts an embodiment of a motor-driven wheel as an omnidirectional wheel in an internal view.
Figure 5:
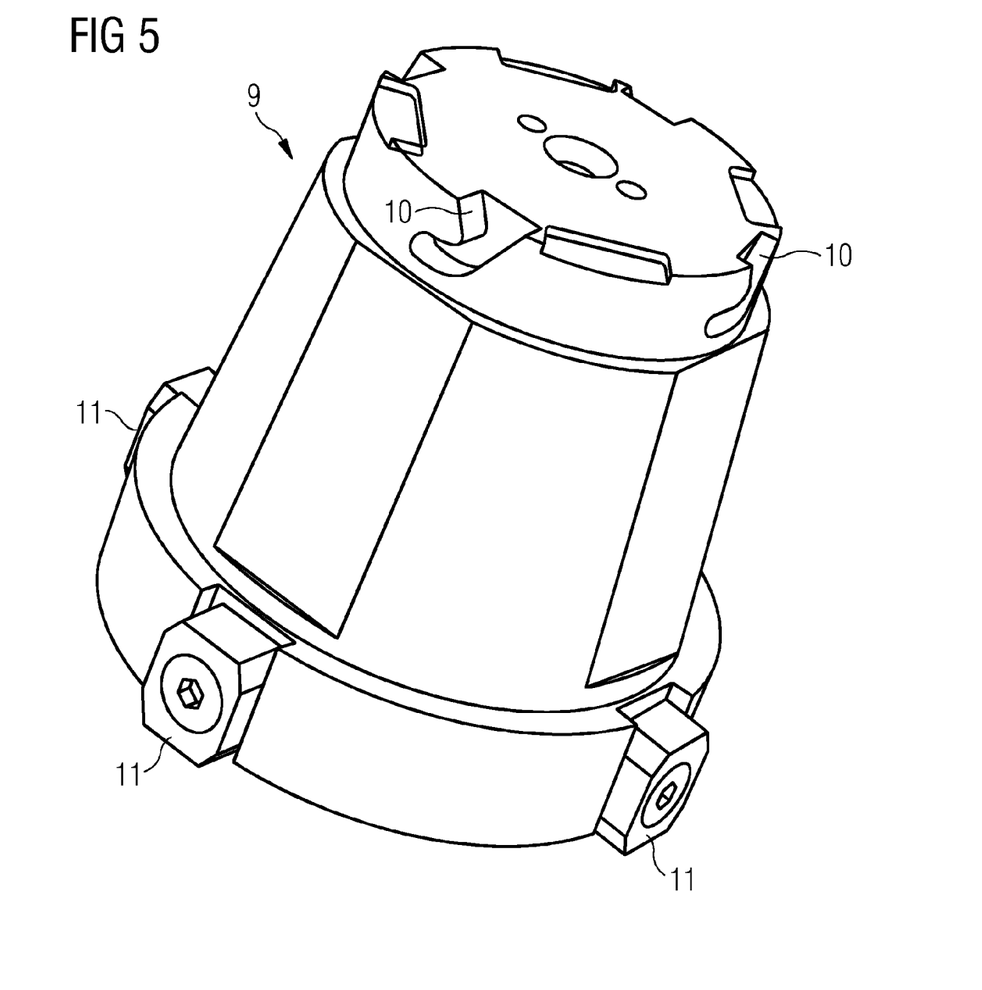
FIG. 5 depicts a perspective view of an embodiment of a hub.

FIG. 4 shows a motor-driven wheel 2 configured as an omnidirectional wheel 15, in an internal view and from its rear side, the rear side being the end side of the motor-driven wheel 2 facing toward the mobile medical device 1. For example, the omnidirectional wheel 15 may be configured as a Mecanum wheel. In this embodiment, in the interior of the motor-driven wheel (e.g., the omnidirectional wheel 15), or in the inner circumference of the motor-driven wheel, a truncated cone-shaped depression 8 is formed. The truncated cone-shaped depression 8 is formed corresponding and precisely fitting to a truncated cone-shaped configuration of the hub 9 (e.g., as shown in FIG. 5 and as will be described in greater detail below). The locking device 5 is shown having guide elements 6. The guide elements 6 may be configured (e.g., as shown in FIG. 4) as pins.

FIG. 5 shows a hub 9 associated with the motor-driven wheel 2. The hub 9 carries, on an outer surface, the motor-driven wheel 2 and in the present exemplary embodiment the hub 9 is configured in a truncated cone-shaped. Formed on the circumference of the hub are grooves 10 and twist-proofing elements 11 that may provide that the motor-driven wheel 2 may not twist relative to the hub 9 in operation or during locking.

Making reference to FIGS. 3, 4 and 5, the functional principle of the removal and placement of the motor-driven wheel 2 relative to the hub 9 will now be described. During a complete changing procedure, the rotatably mounted hub 9 remains on the axle 14 on the chassis. In the context of the wheel change, only the motor-driven wheel 2 is removed, as shown in FIG. 4 with the example of the omnidirectional wheel 15.

Thus, if needed, a complete and gapless cleaning of the motor-driven wheel 2 is possible. For example, the motor-driven wheel 2 may be placed in a washing or cleaning machine typically used in the clinical environment, and cleaned. The motor-driven wheel 2 may also be replaced immediately by an already cleaned motor-driven wheel 2.

The locking device 5 serves for secure removal and fastening of the motor-driven wheel 2 (e.g., in the context of a cleaning of the motor-driven wheel 2).

In one embodiment of the locking device 5, the locking device 5 is configured to be twistable. Here, on the circumference of the hub 9 or in the twistable locking device 5 grooves 10 (e.g., helical grooves) are introduced and simultaneously at the corresponding counterpart (e.g., on the twistable locking device 5 or on the periphery of the hub 9) guide elements 7 are attached. On twisting of the locking device 5, the guide elements 7 cause an axial displacement of the motor-driven wheel 2. Thus during twisting, the locking device 5 displaces and fixes the motor-driven wheel 2 onto the hub 9 or releases the motor-driven wheel 2 from the hub 9 on twisting in the opposite direction.

In another embodiment (not shown) of the locking device 5, the locking and unlocking is provided by locking elements (e.g., balls pressed into the grooves 10 that are arranged on the circumference of the hub 9). By an axially displaceable or rotatable sleeve on the motor-driven wheel 2 or in the hub 9, the guide elements 7 are fixed in a locking position.

In a another embodiment (not shown) of the locking device 5, locking is performed with a centrally arranged hinged hook which, on actuation, pulls the motor-driven wheel 2 toward the sleeve described above paragraph and fixes the motor-driven wheel 2. The centrally arranged hinged hook may be configured such that by opposing actuation, the hook unlocks the motor-driven wheel 2 and thus pushes the motor-driven wheel 2 downwardly from the hub 9. For example, for actuation purposes, the gripping element 6 may be configured as a handle and simultaneously configured for carrying the wheel. The gripping element 6 may alone suffice for releasing and carrying.

In order that, on actuation of the locking device 5 when the locking device 5 is configured so as to be twistable, the motor-driven wheel 2 does not twist relative to the hub 9, the hub 5 may be equipped on a circumference of the hub 5 with the at least one twist-proofing element 11, as shown in FIG. 5. One embodiment of the twist-proofing element 11 may be provided with an element protruding (e.g., milled out from or screwed onto the circumference of the hub 9). For example, the protruding element may be configured octagonal.

Corresponding thereto, in the inner circumference of the motor-driven wheel 2, grooves are introduced in which the twist-proofing elements 11 act. If a twist-proofing element 11 and grooves 10 are simultaneously provided on the circumference of the hub 9, twist-proofing element 11 and grooves 10 may respectively be mounted on the different ends of the hub 9. For example, if the hub 9 is configured so as to be truncated cone-shaped, the grooves 10 are then situated on the outer smaller circumference of the hub 9 (e.g., the side facing away from the mobile medical device 1), and the twist-proofing elements 11 are situated at the opposite side, the outer larger circumference (e.g., the side facing away from the mobile medical device 1).

The fold-out gripping element 6 of the locking device 5 serves to actuate the locking device 5. The fold-out gripping element 6 may be configured as a fold-out handle so that the unlocked and removed motor-driven wheel 2 may be carried, without an inconvenient change of grip, directly on the gripping element 6. Thus, the motor-driven wheel 2 may be removed with bare hands and without any additional aids, such as tools.

The fold-out gripping element 6 may be configured such that the fold-out gripping element may be folded in only with a motor-driven wheel 2 mounted in its starting position if the locking device 5 is in a locked end position (e.g., with a firmly mounted motor-driven wheel 2). For example, this may be achieved in the locking position by eccentric cams on the locking device 5 and corresponding depressions on the hub 9. A safety-relevant effect is provided because accidentally incomplete locking of the motor-driven wheel 2 is immediately apparent.

The cover element 4 of the motor-driven wheel 2 may be folded over (e.g., opened) during a wheel change. In one embodiment, the folding-back into the starting position (e.g., the closed position) of the cover element 4 is only possible if the motor-driven wheel 2 is pushed completely onto the correct axial position of the hub 9 and the gripping element 7 of the locking device 5 is folded in.

Although the invention has been illustrated and described in detail based on the preferred exemplary embodiments, the invention is not restricted by the examples given and other variations can be derived therefrom by a person skilled in the art without departing from the protective scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A mobile medical device comprising:
   a motor-driven wheel configured to move the mobile medical device;
   a hub associated with the motor-driven wheel, wherein the motor-driven wheel is configured to be arranged on the hub;
   a locking device configured to connect the motor-driven wheel to the hub and to release the motor-driven wheel from the hub;
   grooves in the locking device, wherein the locking device is configured to rotate;
   corresponding guide elements on a circumference of the hub to engage in the grooves; and
   a handle on the locking device, wherein the handle is arranged on an end face of the motor-driven wheel facing away from the mobile medical device,
   wherein the handle is configured to rotate about an axis between a first position and a second position, wherein the handle extends out from the end face of the motor-driven wheel in the first position, and wherein the handle is positioned adjacent to the end face of the motor-driven wheel in the second position,
   wherein the locking device is configured to be twisted in a first direction by hand using the handle to remove the motor-driven wheel and the locking device from the hub, and
   wherein the locking device is configured to be twisted in a second, opposite direction by hand using the handle to attach the motor-driven wheel and the locking device to the hub.

2. The mobile medical device of claim 1, wherein the motor-driven wheel is an omnidirectional wheel.

3. The mobile medical device of claim 1, further comprising:
   an axle on which the hub is arranged and rotatably mounted.

4. The mobile medical device of claim 1, wherein the locking device and the hub are configured such that the handle is configured to be positioned in the second position only when the motor-driven wheel is in a locked position.

5. The mobile medical device of claim 1, further comprising:
   a lifting apparatus configured to lift the motor-driven wheel from a floor surface.

6. The mobile medical device of claim 5, further comprising:
at least one non-motor-driven wheel, the non-motor-driven wheel configured to support the mobile medical device on the floor surface when the motor-driven wheel has been lifted from the floor surface.

7. The mobile medical device of claim 1, wherein the hub is configured to be truncated cone-shaped, and
wherein the motor-driven wheel has a corresponding truncated cone-shaped depression.

8. The mobile medical device of claim 1, further comprising:
at least one twist-proofing element arranged on a circumference of the hub, the twist-proofing element configured to hold the motor-driven wheel in a twist-proof manner on the hub.

9. The mobile medical device of claim 2, further comprising:
at least four omnidirectional wheels configured as Mecanum wheels.

10. A mobile medical device comprising:
a motor-driven wheel configured to move the mobile medical device;
a hub associated with the motor-driven wheel, wherein the motor-driven wheel is configured to be arranged on the hub;
an axle on which the hub is arranged and rotatably mounted;
a locking device configured to connect the motor-driven wheel firmly to the hub and to release the motor-driven wheel from the hub;
a handle on the locking device, wherein the handle is arranged on an end face of the motor-driven wheel facing away from the mobile medical device;
grooves on a circumference of the hub; and
corresponding guide elements of the locking device configured to engage in the grooves,
wherein the handle is configured to rotate about an axis between a first position and a second position, wherein the handle extends out from the end face of the motor-driven wheel in the first position, and wherein the handle is positioned adjacent to the end face of the motor-driven wheel in the second position, and
wherein the locking device is configured to rotate to: (1) disengage the guide elements from the grooves to remove the motor-driven wheel from the hub by hand using the handle, or (2) engage the guide elements in the grooves to attach the motor-driven wheel to the hub by hand using the handle.

11. The mobile medical device of claim 10, wherein the motor-driven wheel is an omnidirectional wheel.

12. The mobile medical device of claim 10, wherein the locking device and the hub are configured such that the handle is configured to be positioned in the second position only when the motor-driven wheel is in a locked position.

13. The mobile medical device of claim 10, further comprising:
a lifting apparatus configured to lift the motor-driven wheel from a floor surface.

14. The mobile medical device of claim 13, further comprising:
at least one non-motor-driven wheel, the non-motor-driven wheel configured to support the mobile medical device on the floor surface when the motor-driven wheel has been lifted from the floor surface.

15. The mobile medical device of claim 10, further comprising:
at least one twist-proofing element arranged on a circumference of the hub, the twist-proofing element configured to hold the motor-driven wheel in a twist-proof manner on the hub.

16. A mobile medical device comprising:
a motor-driven wheel configured to move the mobile medical device;
a hub associated with the motor-driven wheel, wherein the motor-driven wheel is configured to be arranged on the hub;
a locking device configured to connect the motor-driven wheel firmly to the hub and to release the motor-driven wheel from the hub;
a handle on the locking device, wherein the handle is arranged on an end face of the motor-driven wheel facing away from the mobile medical device;
an axle on which the hub is arranged and rotatably mounted; and
an electric motor arranged in the axle, the electric motor configured to drive the motor-driven wheel,
wherein the handle is configured to rotate about an axis between a first position and a second position, wherein the handle extends out from the end face of the motor-driven wheel in the first position, and wherein the handle is positioned adjacent to the end face of the motor-driven wheel in the second position,
wherein the motor-driven wheel is configured to be reversibly removed from the hub and placed on the hub by hand using the handle and without aids.

17. The mobile medical device of claim 16, further comprising:
a lifting apparatus configured to lift the motor-driven wheel from a floor surface.

18. The mobile medical device of claim 16, wherein the locking device and the hub are configured such that the handle is configured to be positioned in the second position only when the motor-driven wheel is in a locked position.

19. The mobile medical device of claim 16, wherein the motor-driven wheel is an omnidirectional wheel.

20. The mobile medical device of claim 17, further comprising:
at least one non-motor-driven wheel, the non-motor-driven wheel configured to support the mobile medical device on the floor surface when the motor-driven wheel has been lifted from the floor surface.

* * * * *